(12) United States Patent
Naito

(10) Patent No.: US 9,134,292 B2
(45) Date of Patent: Sep. 15, 2015

(54) METHOD FOR SIMULATING RUBBER MATERIAL

(75) Inventor: Masato Naito, Kobe (JP)

(73) Assignee: Sumitomo Rubber Industries, Ltd., Kobe-shi (JP)

( * ) Notice: Subject to any disclaimer, the term of this patent is extended or adjusted under 35 U.S.C. 154(b) by 419 days.

(21) Appl. No.: 13/695,519

(22) PCT Filed: May 17, 2011

(86) PCT No.: PCT/JP2011/061329
§ 371 (c)(1),
(2), (4) Date: Oct. 31, 2012

(87) PCT Pub. No.: WO2011/145621
PCT Pub. Date: Nov. 24, 2011

(65) Prior Publication Data
US 2013/0054208 A1    Feb. 28, 2013

(30) Foreign Application Priority Data

May 20, 2010  (JP) .................................. 2010-116597

(51) Int. Cl.
*G06F 7/60*    (2006.01)
*G01N 33/44*    (2006.01)

(52) U.S. Cl.
CPC ..................................... *G01N 33/445* (2013.01)

(58) Field of Classification Search
None
See application file for complete search history.

(56) References Cited

U.S. PATENT DOCUMENTS

| | | | |
|---|---|---|---|
| 4,945,964 A * | 8/1990 | Takiguchi et al. | 152/209.5 |
| 6,269,690 B1 * | 8/2001 | Shimizu et al. | 73/146 |

(Continued)

FOREIGN PATENT DOCUMENTS

| | | |
|---|---|---|
| JP | 2005-121535 A | 5/2005 |
| JP | 3668238 B2 | 7/2005 |

(Continued)

OTHER PUBLICATIONS

Raos et al. ("Computational Experiments on Filled Rubber Viscoelasticity: What Is the Role of Particle-Particle Interactions?", American Chemical Society, 2006, pp. A-H).*

(Continued)

*Primary Examiner* — Omar Fernandez Rivas
*Assistant Examiner* — Iftekhar Khan
(74) *Attorney, Agent, or Firm* — Birch, Stewart, Kolasch & Birch, LLP

(57) ABSTRACT

A method for simulating a rubber material comprises a step of setting a rubber material model modeled on a rubber material including rubber, silica, and an interface bonding agent to bond them with numerically analyzable elements; a step of calculating deformation by setting conditions in the rubber material model; and a step of acquiring needed physical quantity from the deformation calculation. The rubber material model (2) comprises a matrix model (3) modeled on a rubber matrix, a plural of silica models (4) modeled on the silica arranged in said matrix model (3), and an interface model (5) surrounding annularly each of the silica models (4) and having a harder physical property than the matrix model. The rubber material model comprises a coupled body formed by coupling a plural of the silica models (4) via the interface model (5).

2 Claims, 14 Drawing Sheets

(56) References Cited

U.S. PATENT DOCUMENTS

| | | | |
|---|---|---|---|
| 2005/0086034 A1 | 4/2005 | Naito et al. | |
| 2006/0106586 A1* | 5/2006 | Naito | 703/2 |
| 2006/0136151 A1* | 6/2006 | Shiraishi | 702/42 |
| 2010/0032071 A1* | 2/2010 | Miyazaki | 152/525 |
| 2010/0041793 A1* | 2/2010 | Pierik et al. | 523/205 |
| 2010/0076151 A1* | 3/2010 | Datta et al. | 524/571 |
| 2011/0046290 A1* | 2/2011 | Toyoda et al. | 524/525 |
| 2011/0112215 A1* | 5/2011 | Kojima | 523/158 |
| 2011/0288838 A1* | 11/2011 | Hamatani et al. | 703/6 |
| 2012/0048444 A1* | 3/2012 | Miyazaki | 152/543 |

FOREIGN PATENT DOCUMENTS

| | | |
|---|---|---|
| JP | 2009-216612 A | 9/2009 |
| JP | 2010-2314 A | 1/2010 |
| JP | 2010-205165 A | 9/2010 |

OTHER PUBLICATIONS

Wu et al. ("Multiaxial and Time Dependent Behavior of a Filled Rubber", Kluwer Academic Publishers, 2001, pp. 293-331).*

Zaimova et al. ("Elastomeric matrix composites: effect of processing conditions on the physical, mechanical and viscoelastic properties", Journal of Achievements in Materials and Manufacturing Engineering vol. 50 Issue 2 Feb. 2012, pp. 81-91).*

Arruda, et al. "A Three-Dimensional Constitutive Model for the Large Stretch Behavior of Rubber Elastic Materials", Journal of the mechanics and Physics of Solids, vol. 41 Issue 2, pp. 389-412, (Feb. 1993).

Internaitonal Search Report mailed on Aug. 23, 2011, issued in PCT/JP2011/061329.

Kilian H-G. et al., "Large deformation in filled networks of different architecture and its interpretation in terms of the van der Waals network model", Colloid Polym. Sci., 1987, vol. 265, No. 5, pp. 410-423.

Kitamura et al., "Bunshisa Amime Riron ni Motozuku Silica Juten Gomu no Nendansei Kyodo no Simulation ni yoru Hyoka", The Japan Society of Mechanical Engineers Keisan Rikigaku Koenkai Ronbunshu (CD-ROM), 2008, vol. 21st, p. Rombunno.109.

Kitamura et al., "Bunshisa Amime Rironni Motozuku Silica Juten Gomu no Kaimen Tokusei-no Model-ka to Simulation ni yoru Hyoka", The Japan Society of Mechanical Engineers Keisan Rikigaku Koenkai Ronbunshu (CD-ROM), Oct. 9, 2009, vol. 22nd, p. Rombunno.915.

Ladouce-Stelandre et al., "Dynamic Mechanical Properties of Precipitated Silica Filled Rubber: Influence of Morphology and Coupling Agent", Rubber Chem. Technol., 2003, vol. 76, No. 1, p. 145-159.

Mele at al., "Analysis of the Viscoelastic Behaviour of Silica Filled Rubber: Prediction of the Interphase Properties", Macromol. Symp., 2003, vol. 194, p. 185-190.

Mochizuki et al., "Gel-so Network Kozo o Teishita Silica Juten Gomu no Model-ka to Suchi Simulation", The Japan Society of Mechanical Engineers Keisan Rikigaku Koenkai Ronbunshu (CD-ROM), Oct. 9, 2009, vol. 22nd, 3 pages.

Mochizuki et al., "Modeling and Simulation of Viscoelastic Defomation Behavior of Silica-Filled Rubber with Network like Structure in Gel Phase", The Japan Society of Mechanical Engineers M&M Zairyo Rikigaku Conference (CD-ROM), vol. 2009, 3 pages.

* cited by examiner

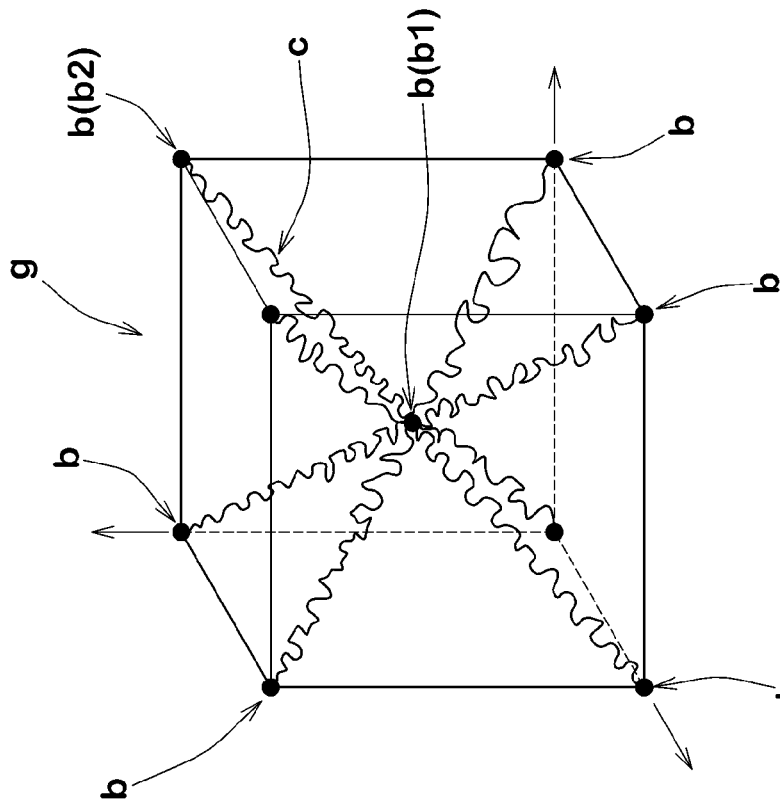

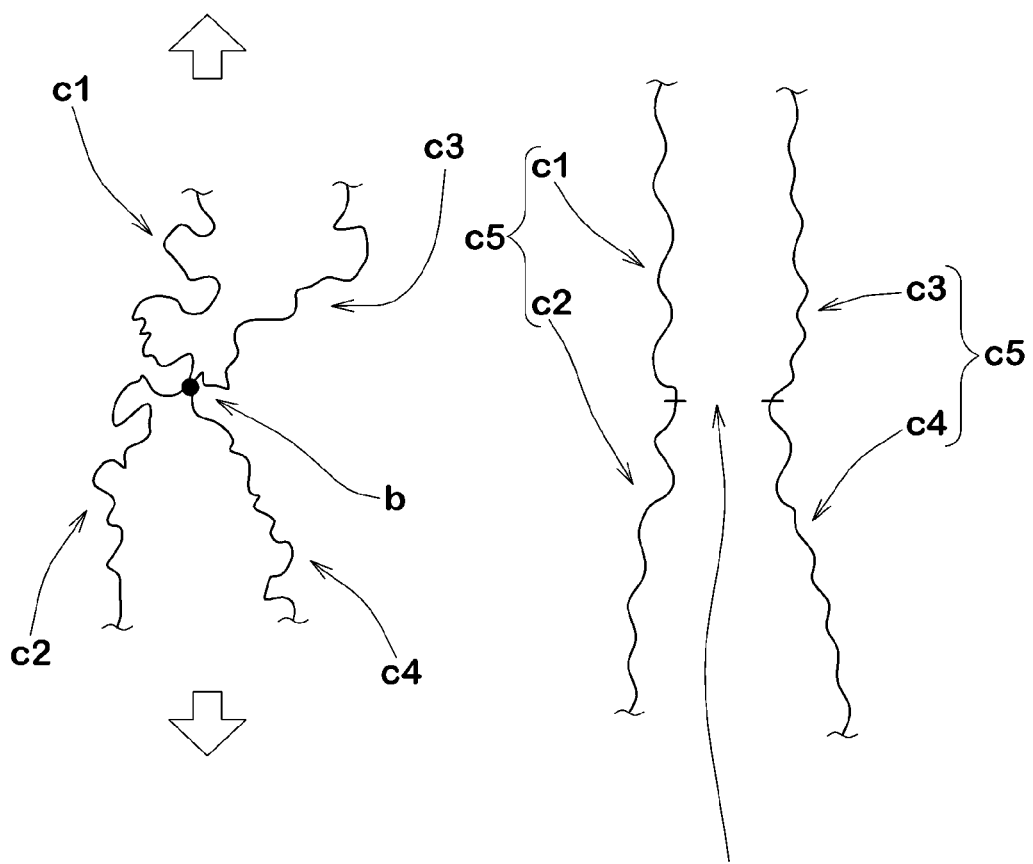
Disappearance of junction point (a) Relation between interface bonding agent and peak temperature of tan δ

(b) Relation between sulfur content of vulcanized rubber and peak temperature of tan δ

(a) Model 1 (Example 1)

(c) Model 3 (Example 2)

(b) Model 2 (Comparative Example 1)

(d) Model 4 (Comparative Example 2)

(e) Model 5 (Example 3)

METHOD FOR SIMULATING RUBBER MATERIAL

TECHNICAL FIELD

The present invention relates a method for simulating a rubber material helping an analysis of deformation of the rubber material comprising a matrix rubber, silica, and interface bonding agent which bonds them with high accuracy.

BACKGROUND OF THE INVENTION

In a rubber material for a tire, sporting-goods, and other industrial products, carbon was traditionally in heavy usage to improve its mechanical trait. In recent years, silica has been in heavy usage in place of the carbon. That is why silica compound has a lower energy loss than carbon compound, and it helps to reduce rolling resistance of the tire and to improve fuel efficiency, for example. Moreover, the silica is non-oil resource and eco-friendly filler. Therefore, a computer simulation analysis of deformation of the rubber material compounding silica with high accuracy is very beneficial for future development tires and the like.

In general, the following Non-Patent Document 1 and Patent Document 1 are known as a method for simulating the rubber material with a computer. Patent Document 1 discloses a deformation calculate in a finite element method by setting a matrix model and a filler model, as a rubber material model, modelized with numerically analyzable elements taking into account of an influence of the filler.

RELATED ART DOCUMENTS

Patent Document

Patent Document 1: Japan Patent Publication 3668238.
Non-Patent Document 1: Ellen M. Arruda and Marry C. Boyce, "A THREE-DIMENSIONAL CONSTITUTIVE MODEL FOR THE LARGE STRECH BEHAVIOR OF RUBBER ELASTIC MATERIALS", Journal of the Mechanics and Physics of Solids Volume 41, Issue 2, pp. 389-412 (February 1993).

SUMMARY OF THE INVENTION

Problem to be Solved by the Invention

As shown in FIG. 15, when simulating the rubber material compounding silica, a rubber material model 20 was used, which comprised a matrix model 21 modeled on a rubber matrix, a silica model 22 modeled on silica arranged therein in a variance geometry, and an interface model 23 surrounding annularly the periphery of a surface of the silica models 22.

In the matrix model 21 and the silica models 22, each physicality was prospectively defined. For example, the silica model 22 was used as a hard elastic body, in which an elastic modulus was set. As the physicality in the matrix model 21, physicality (a function demonstrating a relation between a stress and an stretch, for example) was set on results of a tensile test of so-called a rubber without filler.

Into the rubber material compounding silica, an interface bonding agent such as a silane coupling agent and the like was compounded so as to bond the silica and the rubber. Therefore, a conventional simulation was on the premise of that the silica and the rubber were bonded with the interface bonding agent. And, an interface between the silica model 22 and the matrix model 21 was determined as an interface model 23.

However, when simulating the tensile deformation with the use of the rubber material model 20, for example, the stress-stretch test result might greatly differ the stress-stretch result obtained from a real tensile test. However, an inventor of the present invention discovered through various tests that the gap between these results caused of a geometry of silica models.

That is to say, the inventor earnestly studied about the geometry of silica and made a hypothesis that the interface bonding agent did not only adhere the silica and the matrix rubber but also confine a movement of a silica particle by connecting the silica and the silica to each other in cord-like fashion. After simulating in accordance with such a model, the inventor found a very high correlativity between the simulational test result and the real test result, and he achieved the present invention.

Thus, It is an object of the present invention to provide the simulation method capable of calculating the deformation of the rubber member compounding silica with high accuracy.

The present invention relates to a method for simulating a rubber material comprising a step of setting a rubber material model modeled on a rubber material including a matrix rubber, silica, and an interface bonding agent to bond them with numerically analyzable elements; a step of calculating deformation by setting conditions in the rubber material model; and a step of acquiring a needed physical quantity from the deformation calculation. The rubber material model comprises a matrix model modeled on the matrix rubber; a plural of silica models modeled on the silica arranged in the matrix model; and an interface model surrounding annularly each of the silica models and having a harder physical property than the matrix model. The rubber material model comprises a coupled body formed by coupling a plural of the silica models via the interface model.

According to the present invention, the rubber material model comprises a matrix model modeled on a rubber matrix; a plural of silica models modeled on the silica arranged in the matrix model; and an interface model surrounding annularly each of the silica models and having a harder physical property than the matrix model. The rubber material model includes a coupled body connected with a plural of silica models via interface model. By conducting a simulation (deformation calculation) with use of such a rubber, one can obtain a very highly calculation result correlated with a deformation behavior of a real rubber material compounding silica.

The coupled body preferably extends continuously with respect to an arbitral direction of axis in the entire range of the region of the rubber material model.

The step of setting the rubber material model comprises a parameter determination process to determine a parameter of physicality in the interface model. The parameter determination process comprises a process of preparing at least a first unvulcanized rubber composition having the same compound as the rubber material model of an analysis object, and a second unvulcanized rubber composition having a compound excluding an interface bonding agent from the first unvulcanized rubber composition;

a process of obtaining first and second residues to obtain the first and second residues removing the matrix rubber from the first and second unvulcanized rubber compositions, respectively, by immersing the first and second unvulcanized rubber composition into a solvent;

a process of estimating a difference T2−T1 on the basis of these two peak temperatures by measuring at least a peak temperature T2 of tan δ of the second residue and a peak temperature T1 of tan δ of the first residue and estimate;

a process of preparing a basic vulcanized rubber material having a compound excluding silica from the first unvulcanized rubber composition, and different kinds of vulcanized rubber materials having a difference only in crosslink density from the basic vulcanized rubber material;

a process of obtaining a relation between the peak temperature of tan δ of the vulcanized rubber material and the crosslink density by measuring each of the peak temperature of tan δ of the vulcanized rubber materials;

a process of specifying crosslink density of the vulcanized rubber material having a peak temperature of tan δ is equivalent to a temperature obtained by adding the difference T2−T1 into a peak temperature T3 of tan δ of the basic vulcanized rubber material from the relation; and a process of defining the parameter of the interface model on the basis of the physicality of the vulcanized rubber material of the identified crosslink density.

BRIEF EXPLANATION OF THE DRAWING

FIG. 4 (B) is a line drawing explaining the molecular chain single structure thereof; FIG. 4 (C) is an enlarged view of the single molecular chain, and FIG. 4 (D) is an enlarged view of a segment.

FIG. 5 (A) is a diagrammatic perspective view showing a reticulation structure body of the viscoelastic material; and FIG. 5 (B) is a diagrammatic perspective view showing an example of an eight-chain model.

FIG. 6 (A) and FIG. 6 (B) are line drawings explaining a tension crack of a junction point of the molecular chain.

EXPLANATION OF THE REFERENCE

Figure 1:
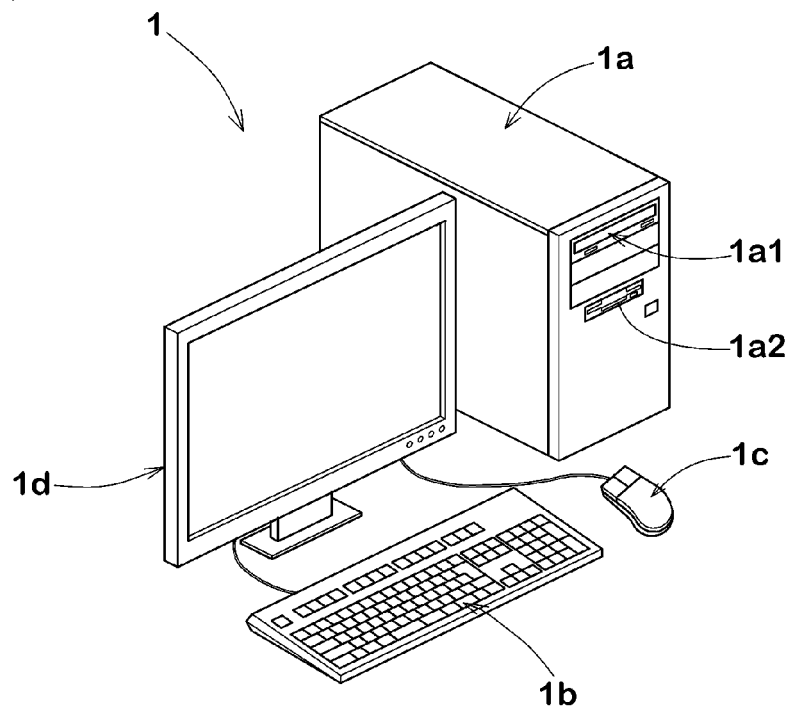
FIG. 1 is a diagrammatic perspective view of a computer device showing an example of the present embodiment.

1 Computer device
2 Rubber material model
3 Matrix model
4 silica model
5 Interface model
6 coupled body

CONFIGURATION OF EXPLOITATION OF INVENTION

Hereinafter, an embodiment of the present invention will be described with referent to the drawings.

FIG. 1 shows a computer device 1 to conduct a simulation method of the present invention. This computer device 1 comprises a main portion 1a, a keyboard 1b, a mouse 1c and a display apparatus 1d. Inside the main portion 1a, there is a large-capacity storage device such as a CPU, a ROM, a working memory, and a magnetic disk and the like. The main portion 1a comprises a CD-ROM and a flexible disk drive apparatuses 1a1 and 1a2. Thus, the main portion 1a stores processing procedures (program) in the large-capacity storage device to execute the after-mentioned simulation method of the present invention.

In the simulation method of the present embodiment, the deformation of the rubber material compounding silica, which comprises the matrix rubber, the silica, and the interface bonding agent bonding them is simulated.

An example of the interface bonding agent used in the present embodiment is a silane coupling agent. Examples of the silane coupling agent are as follows:

bis(3-triethoxysilylpropyl)polysulfide,
bis(2-triethoxysilylethyl)polysulfide,
bis(3-trimethoxysilylpropyl)polysulfide,
bis(2-trimethoxysilylethyl)polysulfide,
bis(4-triethoxysilylbutyl)polysulfide,
bis(4-trimethoxysilylbutyl)polysulfide and the like.

These silane coupling agents can be used independently, and also not less than two kinds of them can be used in combination. Especially, in terms of compatibility of an effect of addition of the coupling agent and cost, bis(3-triethoxysilylpropyl)disulfide and the like are preferably used.

Figure 2:
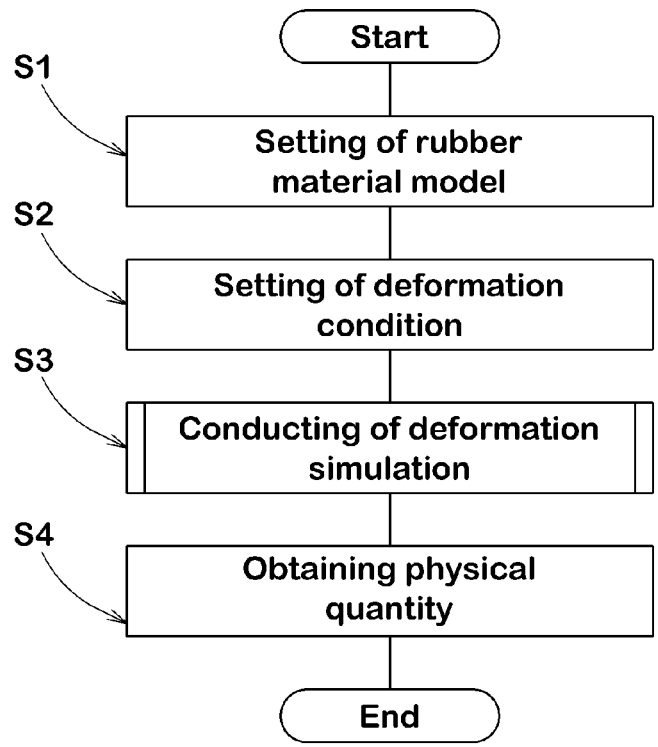
FIG. 2 is a flowchart showing operating procedures of the present embodiment.

FIG. 2 shows an example of operating procedures of the simulation method of the present embodiment. In the present embodiment, first of all, a model of the rubber material is set (step s1).

Figure 3:
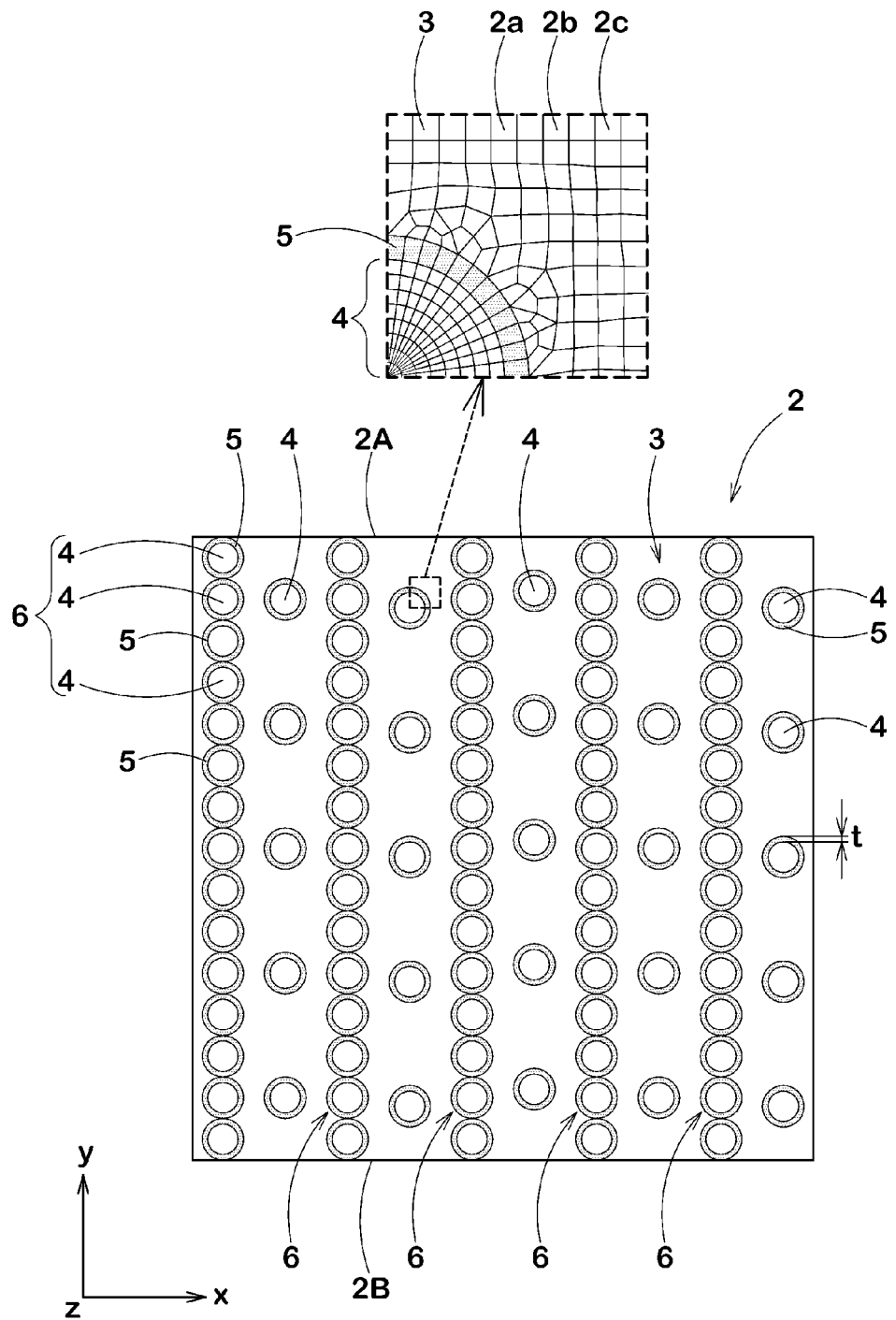
FIG. 3 is a line drawing showing an embodiment of the rubber material model (microscopic structure).

FIG. 3 shows an example of a visualized rubber material model 2 as a minimum repetition unit of the microscopic structure. In the rubber material model 2, a very little region of the rubber material compounding silica to be analyzed is replaced with finite numbers of small elements (mesh) 2a, 2b, 2c . . . . The respective elements 2a, 2b, 2c . . . are defined to be capable of numerical analysis.

The above-mentioned numerical analytical possibility means that the deformation calculation of each element or of the whole of a system can be analyzed by a numerical analytical approach such as a finite element method, a finite volume method, a method of finite difference or a boundary element method, for example. More particularly, regarding the respective elements 2a, 2b, 2c . . . , a coordinate value at a nodal point, an element configuration, a material property and the like in a coordinate system are defined. For the respective elements 2a, 2b, 2c . . . , elements of a triangular shape or a quadrilateral are preferably used in a two-dimensional surface, for example; and elements of a tetrahedral shape or a hexahedral shape are preferably used in a three-dimensional surface, for example. The rubber material model 2 therefore forms numerical data capable of handling with the above-mentioned computer device 1.

As respects the rubber material model 2 of this embodiment, an analysis of a plane strain state in the deformation simulation described below is analyzed; to be more specific, a tensile deformation in the y-axis direction is simulated. In other word, in the present embodiment, the simulation in the two dimensions without strain in the z-axis direction is done. In this embodiment, the rubber material model 2 as a microscopic structure is a quadrate having 300 nm×300 nm, for example.

The rubber material model 2 of the present embodiment comprises
a matrix model 3 modeled on the matrix rubber part,
a silica models 4 arranged in this matrix model 3 and modeled on the silica, and
an interface model 5 surrounding the annually the each silica model 4 and having defined a harder physical property than the matrix model 3.

The matrix model 3 forms the major portion of the rubber material model 2, for example, and is expressed with use of a plural of elements in the triangular shape or the quadrilateral shape. To perform the calculating deformation, in each of the elements forming the matrix model 3, the relation between the stress and stretch is defined as physicality. In the method for simulating the rubber material of the present embodiment, to express a rubber elasticity reply, the matrix model 3 and the rubber portion of the interface model 5 are calculated on the basis of a molecular chain reticulation theory, respectively.

Figures 4A, 4B, 4C, 4D:
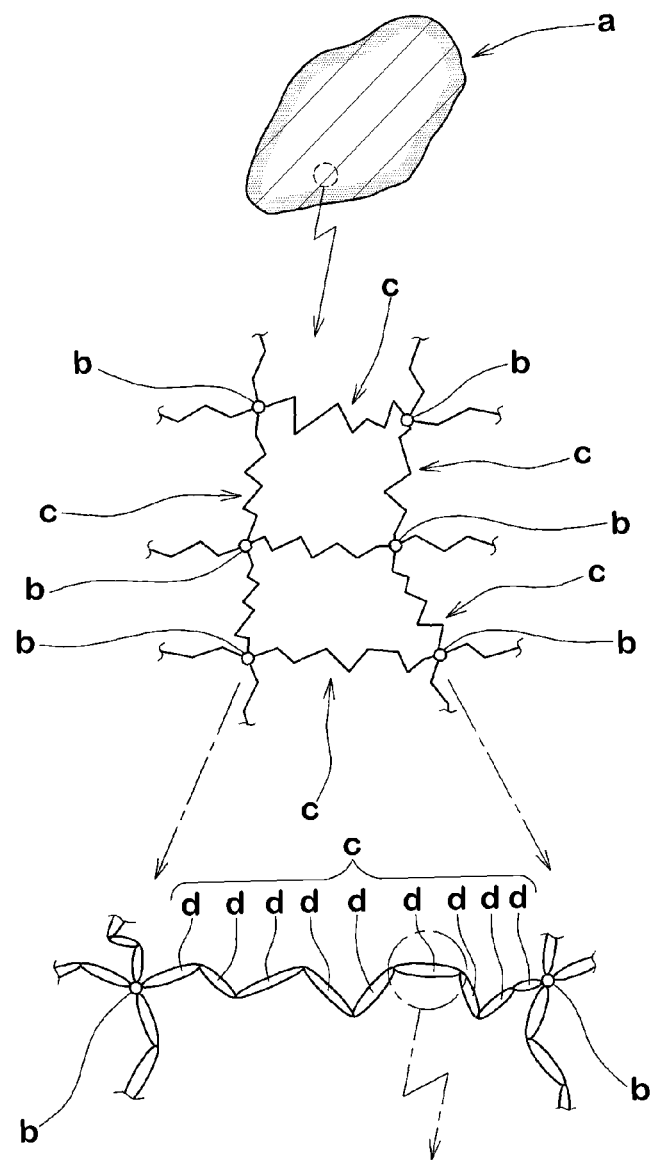
FIG. 4 (A) is a viscoelastic material.

The molecular chain reticulation theory is described briefly as follows: As shown in FIG. 4 (A) and FIG. 4 (B), the molecular chain reticulation theory is based on the premise that the rubber material (a) as a continuum body has a reticulation structure as a microscopic structure, in which a disorderly-oriented molecular chain (c) is connected at a junction point (b). The junction point (b) is an intermolecular scientific bonding, for example, and includes a cross-link point and the like.

In the molecular chain reticulation theory, an average point of the junction point (b) is defined to remain static in the long term with respect to a fluctuation period of an atom, and a perturbation around the junction point (b) is ignored. An end-to-end vector (end-to-end vector) of the molecular chain (c) comprising two junction points (b) and (b) in axially outer edges is assumed to become covariant form with the continuum body of the rubber material where the end-to-end vector are embedded.

The single molecular chain (c) is formed of a plurality of segments (d) as shown in FIG. 4 (C). The each segment (d) scientifically corresponds to a connected body formed of a plural of monomers (f), which is formed of carbon atoms connected by covalent binding as shown in FIG. 4 (D). Each of the carbon atoms rotates freely around the bond axis of the atoms one another, and the segment (d) serpentines in its entirety and the like, and may have various configurations. When the number of the monomer (f) is much enough, the macroscopic property of the segment (d) stays constant through the scaling law, and the single segment (d) is treated as a repeating minimum building unit in the molecular chain reticulation theory. The configuration of the molecular chain defined by the two junction points (b) and (b) shown in FIG. 4 (C) is distribute in accordance with the non-Gaussian statistic distribution. Therefore, a stress σ that generates when adding a stretch (stretch) λ in the direction connecting together the two junction points (b) and (b) is expressed by the following Formula (1).

[Number 1]

$$\sigma = k_B T \sqrt{N} L^{-1}\left(\frac{\lambda}{\sqrt{N}}\right)$$ Formula (1)

$k_B$: Boltzmann constant
$T$: Absolute temperature
$\lambda$: Stretch
$N$: Average segment number per molecular chain
Function $L(x)$: Langevin function defined with the following formulæ

$$L(x) = \frac{d}{dx}\left\{\ln\left(\frac{\sinh x}{x}\right)\right\} = \coth x - \frac{1}{x}$$

Thus, the general responsive property of the reticulation structure can be obtained in view of contribution of the individual molecular chains, but it is mathematically difficult to calculate accurately with careful consideration for all of them. For this reason, in the molecular chain reticulation theory, an averaging means is put in place. The present embodiment is based on the molecular chain reticulation theory with use of the eight-chain model. That is to say, in this means as shown in FIG. 5 (A), the rubber material of the hyperelastic body is assumed to be macroscopically a cube-shaped reticulation structure body formed of assembled minim eight-chain models (g) .... A single eight-chain model (g) is, as shown enlargedly in FIG. 5 (B), assumed that the molecular chain (c) extends from a single junction point b1 defined at the center of the cube to respective eight junction points b2 arranged on respective vertexes, and is calculated.

In the molecular chain reticulation theory of the present embodiment, a disappearance of the junction point (b) according to the strain of the material is taken into account. In the real rubber material, in a deformation process with load, it is known that a twisted together portion of the molecular chain (that is to say, the junction point (b)) disappears by a large strain. In other word, the number of the junction points (b) reduces. For example, as shown in FIG. 6 (A), when a tensile stress acts in the direction of an arrow on the molecular chains c1 to c4 jointed at a single junction point (b), the junction point (b) disappears owing to a large strain caused by stretch of the respective molecular chains c1 to c4. Therefore, as shown in FIG. 6 (B), the two molecular chains c1 and c2 becomes a single long molecular chain c5. The same shall apply to the molecular chains c3 and c4. Such a phenomenon is sequentially generated with the increasing of the loaded deformation of the rubber material. The reduction of the number of the junction point (b) causes an increase of the number of the segments in the single molecular chain (c).

And, the above-mentioned phenomenon is applied to a reticulation structure body (h) shown in FIG. 5 (A). The reticulation structure body (h) is formed by bonding (k) number of eight-chain models (g) in the width direction, in the height direction and in the depth direction, respectively. The total number of the junction point (b) included in the reticulation structure body (h) is expressed in a symbol "m" as a "number of tangle"; see the following Formula (2). Similarly, the number of the molecular chain (c) included in the reticulation structure body (h) (that is to say, the number of molecular chains included in the unit volume of the matrix model 3) "n" is expressed as following Formula (3).

$m=(k+1)^3+k^3$ Formula (2)

$n=8k^3$ Formula (3)

If the number k is an enough large number, other than the third-order term of k from the Formula (2) is omitted so as to obtain the following Formula (4). Moreover, according to the relation between the Formulas (3) and (4),
the number of tangle (m) is expressed with use of the number (n) in the following Formula (5).

$m=2k^3$ Formula (4)

$m=n/4$ Formula (5)

The reticulation structure body (h) has no comings and goings of materials before and after a deformation, it can be assumed that the total number $N_A$ of the segment is constant at all times, and the following Formulas (6) and (7) are as follows:

$N_A=n \cdot N$ Formula (6)

$N=N_A/n=N_A/4m$ Formula (7)

The above-mentioned disappearance of the junction point (b) reduces the number of tangle (m) in the matrix model 3 and increases eventually the number of the segment included in the single molecular chain (c). Therefore, in order to introduce the reduction of junction point associated with the above-mentioned loaded deformation (stretch) into the molecular chain reticulation theory with use of the eight-chain model, an average segment number N per molecular chain in the Formula (1) increases as a function of a parameter λc regarding the strain. As an example of the parameter λc regarding this strain, there is a strain, a stretch, a strain speed, or a primary invariant quantity of the stress tensor or a strain. Moreover, the loaded deformation means a deformation, where a strain of the model increases during a minuscule time. The unloaded deformation means a deformation, where the represent strain reduces.

Therefore, in the matrix model 3 of the present embodiment, the average segment number N per molecular chain is defined as the following Formula (8); as a function that the parameter f(λc) corresponding to the strain of the material is added into an initial stage segment number $N_0$ per molecular chain:

$$N(\lambda c) = N_0 + f(\lambda c) \tag{8}$$

The above-mentioned Formula (1) with use of the average segment number N obtained by the Formula (8) can change the stress in depending on the strain of the matrix model 3. The after-mentioned the deformation simulation of the rubber material model 2, with respect to each element of the matrix model 3, the parameter λc is always calculated at the time of the loaded deformation, and they are substituted into the Formula (8). The segment number N of the element is therefore always updated and is incorporated into the simulation.

The above-mentioned silica model 4 is modeled on silica with use of a plural of quadrilateral elements, and is round as a whole. In the present embodiment, all of particle sizes (diameter) of the respective silica models 4 are equal. In a case of the three-dimensional model, the silica model 4 is preferably modeled in a spherical form. The silica has a diameter of about 10 to 300 nm, and is made of a much harder particle than rubber. The silica models 4 are defined with the substantially same physicality as the silica physicality of this analysis object. That is to say, the silica models 4 in the present embodiment are treated not as a viscoelastic body but as an elastic body. Moreover, the number of the particle of the silica models 4 can be determined on the basis of silica amount of composition on the analysis object, the rubber material, for example.

The interface model 5 is modeled on a movement of the silane coupling agent in bonding scientifically the silica with the matrix rubber in order to incorporate into the simulation. The interface model 5 of the present embodiment is set to surround the silica model 4 annularly and continuously with a small thickness (t). Therefore, the inner circumferential surface of the interface model 5 contacts with the outer circumferential surface of the silica models 4. In the present embodiment, the setup condition is not to separate the inner circumferential surface of the interface model 5 from the outer circumferential surface of the silica model 4. However, when a stress generates more than a predetermined value, a condition of the boundary separation between the silica model 4 and the interface model 5 may be set. A major portion of the outer circumferential surface of the interface model 5 contacts with the matrix rubber model 3.

The thickness (t) of the interface model 5 is not in particular restricted, but in view of various experimental result and the like, the thickness (t) is expected to be about 10 to 30% of the diameter of the silica model 4, more preferably, about 15 to 25% in point of a consistency with the real rubber material.

Also in the interface model 5, a relation between stress and stretch is defined in accordance with the above-mentioned Formula (1). The average segment number N of Formula (1) used in the interface model 5 is set to be a fixed value $N_0$ and does not include the term of f(λc) such as applied adopted on Formula (8).

In view of the physicality of the real interface bonding agent, this interface model 5 is set to have a harder physical property than the matrix rubber. In the present embodiment, the initial stage value $N_0$ of the average segment number N of the formula (8) is set to be smaller than the initial stage value $N_0$ applied on the matrix model 3. Then, the interface model is set to have a less stretch than the matrix model 3. In other word, the interface model 5 is set to have a harder physical property (accurately, viscoelastic property) than the matrix model 4. Incidentally, it comes near to stating the obvious that the interface model 5 is softer than the silica model 4.

Figure 7:
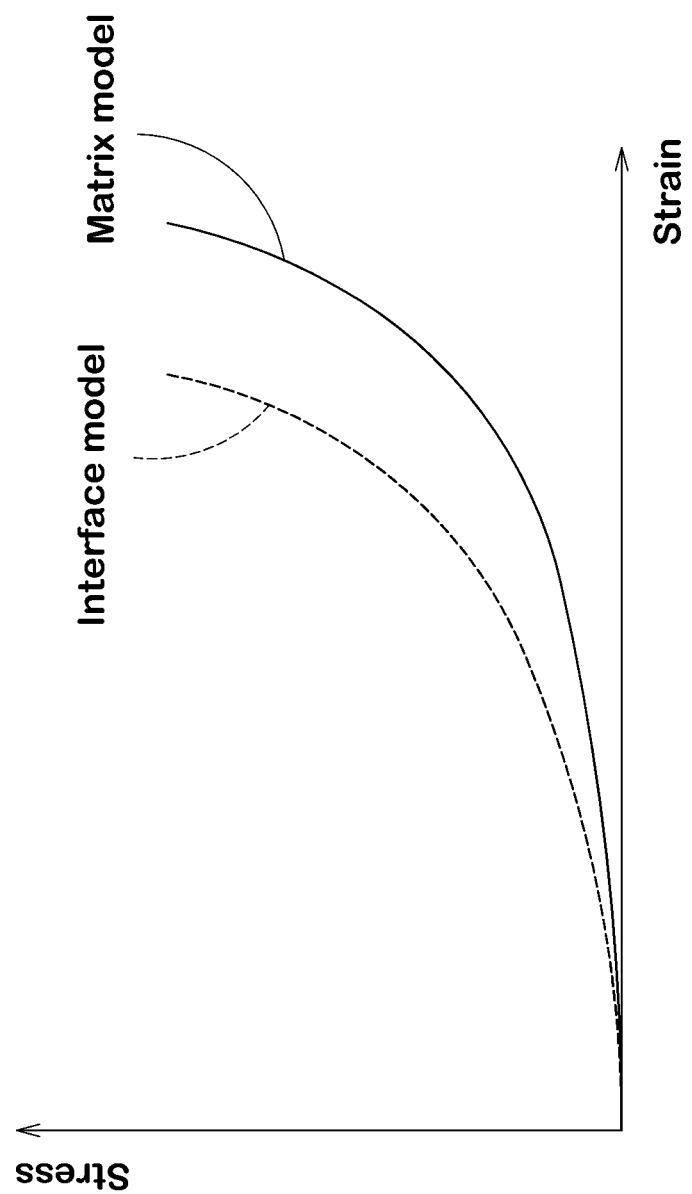
FIG. 7 is a stress-strain curve showing an example of the physicality of a matrix model and an interface model.

The interface model 5 is preferably to set to have a smaller limit stretch than the matrix model 3. In the real rubber material compounding silica, since there is much interface bonding agent between silica particles presumably, it is rational to imagine that the crosslink density thereof is higher than the rubber matrix part. To reflect this condition to the simulation, as shown in FIG. 7, in the case of the interface model 5, a stress starting strain (limit stretch) is preferably set to be smaller than that of the matrix model 3.

The rubber material model 2 comprises a coupled body 6 where a plural of silica models 4 connected via the interface model 5 in a corded-fashion. When measuring silica geometry specifying in various analysis such as measuring with a transmission-type electron microscope, the inventor found that about 30% of the silica particle of the silica compounded rubber has a network structure connecting in the corded-fashion with other silica via the interface bonding agent. It was speculated that such a structure was formed by the interface bonding agents bonding each other in a condensation reaction. It turned out that the interface bonding agent after condensation reaction worked as a crosslink agent and improves the crosslink density around the silica. Therefore, the above-mentioned network structure keeps a distance between the silica particles short and makes resistance to the deformation of the rubber, and owing to a synergetic effect with a reinforce efficacy of the silica particle itself, it is speculated that the entire rubber is much more stiffened. Therefore, to incorporate accurately the geometry of the silica particle in the rubber into the rubber material model 2 brings a more accurate simulation. This efficacy is disclosed in the after-mentioned embodiment.

The coupled body 6 of the present embodiment, relative to an arbitrary axis direction, extends continuously in the entire range of the region of the rubber material model 2. That is to say, each the coupled body 6 of this embodiment extends up and down in a linear arrangement along the axis direction of a tensile direction of the tensile simulation (in this example, y-axis direction). Moreover, it is preferable to provide with a plural of the coupled bodies 6 at intervals in a direction at right angle to the axis line (in this example, x-axis direction). Also, the coupled bodies 6 "extends continuously in the entire range of the region of the rubber material model 2" means that the respective interface models 5*a* and 5*b* of the axially outer edges of the coupled bodies 6 contact with the ends 2A and 2B in an arbitrary direction of the microscopic structure 1 (in this example, the y-axis direction), and the interface models 5 are connected therebetween without termination.

Figure 8:
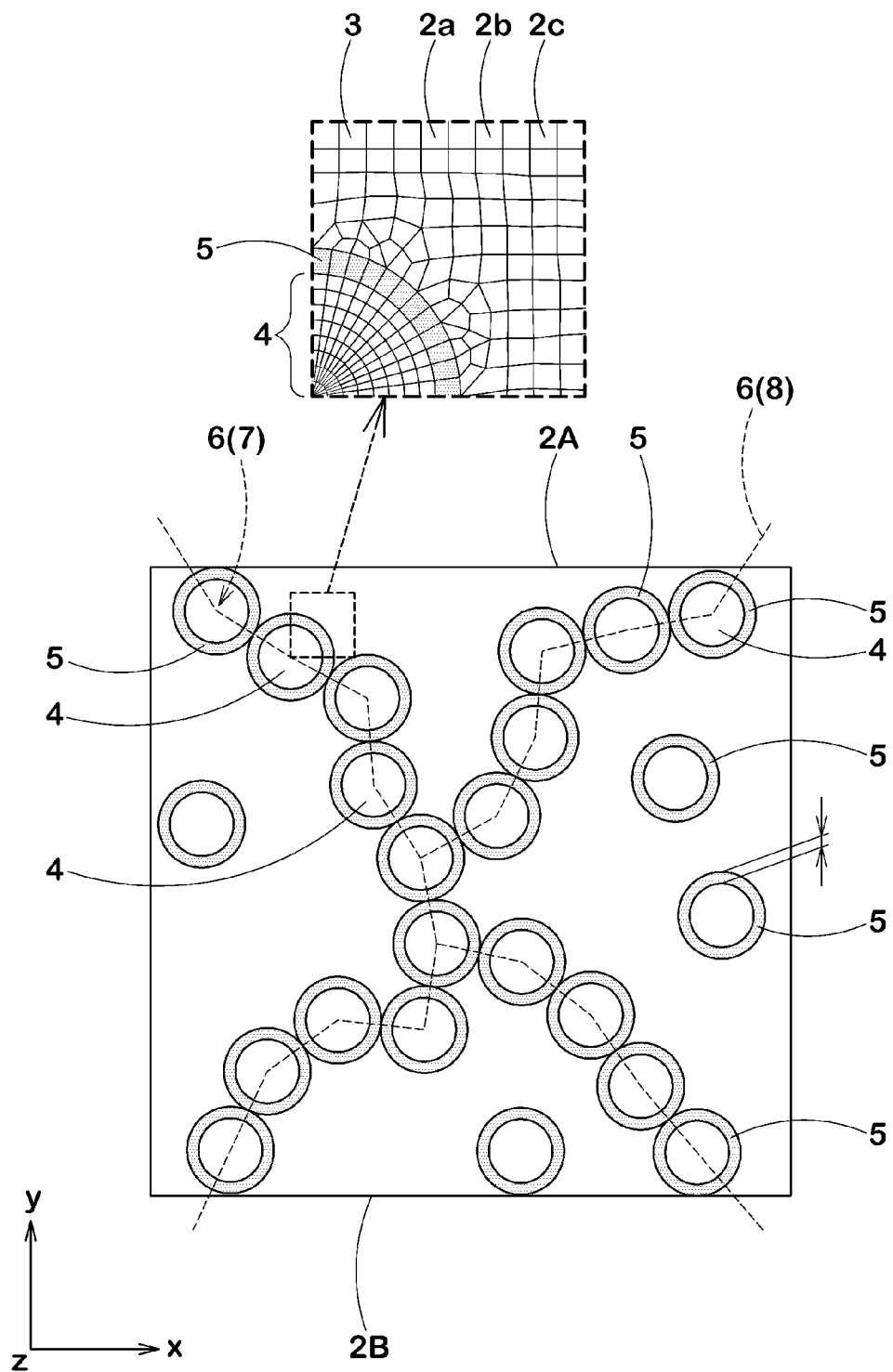
FIG. 8 is a line drawing showing another embodiment of the rubber material model (microscopic structure).

The shape of the coupled body is not limited by the above-mentioned embodiment. As shown in FIG. 8, for example, the coupled body 6 may be formed as a substantially X-shaped random geometry which comprising a first portion 7 extending diagonally right down in the overall region of the y-axis direction in a cell of the microscopic structure, and a second portion 8 crossing with this first portion 7 and extending diagonally left down in the overall region of the y-axis direction. The coupled bodies 6 can be a more complex shape.

With respect to the interface model 5, similar to the matrix rubber 3 and the silica model 4, parameters (density, elastic modulus and the like) regarding the physicality are entered. However, it is realistically difficult to measure directly the physicality of the interface model 5. Conventionally, the parameters regarding the physicality of the interface model 5 were set to have an similar deformation behavior to the silica compounded rubber, which was equivalent to a rubber material model of the analysis object in the simulation (for example, a behavior to obtain a similar result of a tensile test). However, in such a parameter entry, when a test condition differed, calculation accuracy might largely deteriorate. Therefore, in the physicality of the interface model 5 in the present embodiment, its parameter is defined in accordance with a process to be hereinafter described.

First of all, at least a first unvulcanized rubber composition and a second unvulcanized rubber composition are prepared. The first unvulcanized rubber composition having the same compound as the rubber material model of an analysis object. The second unvulcanized rubber composition having a compound in which is formed by excluding only the interface bonding agent from the first unvulcanized rubber composition. In this example, the first unvulcanized rubber composition comprises of the interface bonding agent of 8 wt % and sulfur of 1 phr. The first unvulcanized rubber composition differs the second unvulcanized rubber composition in a presence of the interface bonding agent, and the compositions of the respective residues have the same. In the present embodiment, as a prefer aspect, a plural kinds of other unvulcanized rubber compositions comprising the interface bonding agent of the amount of composition differing from that of the first unvulcanized rubber composition can be prepared. Each of these rubber compositions is prepared to be enough uniformly mixed with a banbury mixer and the like.

With immersion of each of the unvulcanized rubber compositions in a solvent, a process is conducted to obtain a first residue and a second residue after removing matrix rubber from the first unvulcanized rubber composition and the second unvulcanized rubber composition, respectively. For an example, each of the aggregatus unvulcanized rubber compositions is put into a gauze cage of 150 mesh, for example, and is immersed it in toluene for about 48 hours under a condition at room temperature. This makes the matrix rubber elute from each composition into the toluene. Therefore, from the first unvulcanized rubber composition in the gauze cage, obtained are a first residue comprising silica, interface bonding agent, sulfur and other added agents. In contrast, the second unvulcanized rubber composition or another unvulcanized rubber composition in the gauze cage, obtained are the second residue comprising silica, sulfur, and other added agents.

Since the vulcanized rubber cannot elute the matrix rubber into the solvent, a rubber composition before vulcanization is used in the above-mentioned process. Moreover, not substantially or totally involving the matrix rubber, the above-mentioned first residue can be considered as an equivalent to a bound substance of the silica model 4 and the interface model 5 obtained by excepting the matrix model 3 from the rubber material model 2. Therefore, by the use of the first residue as described herein below, the parameter of the interface model 5 can be set more accurately.

In the present embodiment, for example, a viscoelastic test, of the respective residues (in the present embodiment, the first residue, the second residue, and the other residues) is carried out, and each of a peak temperature of tan δ is measured. In this measurement, for example, the residue including mainly the silica and the interface bonding agent resting in the gauze cage is pressed so as to obtain a sample in a bulk state, and a test piece similar to the test piece used in the viscoelastic test of the vulcanized rubber is gotten out of this sample and is measured. Incidentally, the measurement condition of tan δ is as follows:

Initial strain: 10%
Deformation mode: Tension
Frequency: 10 Hz
Half amplitude: 1%

Figure 9A:
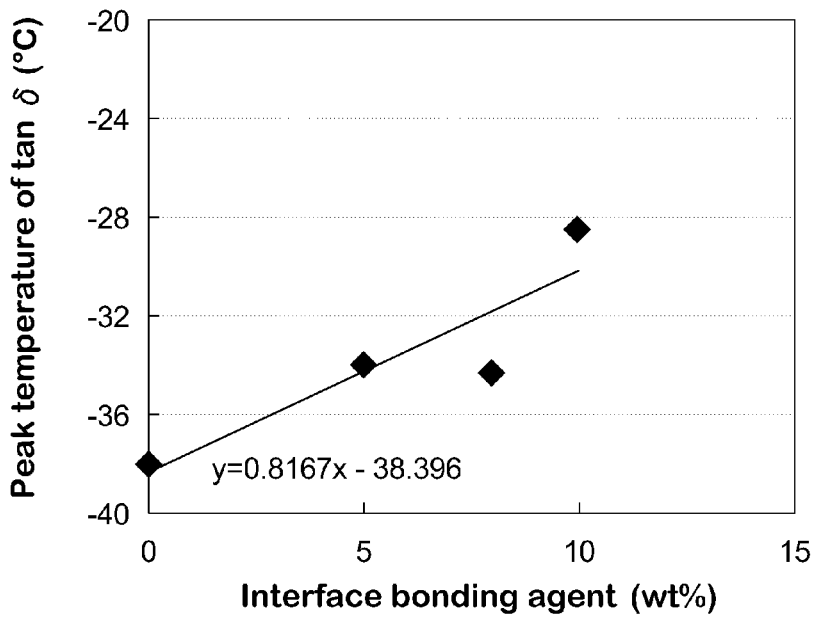
FIG. 9 is a graph demonstrating the relation between tan δ and temperature of a vulcanized rubber uncompounding silica.

Secondly, in the present embodiment, a process is conducted to estimate a difference T2−T1 of the peak temperatures on the basis of the test result of the peak temperatures of the above-mentioned measured tan δ. A graph representation in FIG. 9(a) represents the relation between the peak temperature of tan δ and the amount of composition of the interface bonding agent on the subject of each of the residues. In this embodiment, by performing a linear approximation on the subject of the obtained data, calculated is an approximation straight-line showing the relation between the peak temperature of the tan δ of the residue and the interface bonding agent. The approximation straight-line is presented as follows:

$$y=0.8167x-38.396$$

Also to improve an accuracy of the approximation straight-line, it is preferable to comprise other residues as the present embodiment. Moreover, with the use of the approximation straight-line, the difference T2−T1 between the peak temperature T2 of the tan δ of the second residue and the peak temperature T1 of the tan δ of the first residue is estimated to be 6.5336 deg. C. However, it comes near to stating the obvious that the estimate process of estimating the difference T2−T1 of the temperatures may not only be expressed in the approximation straight-line but also in a second-order or more approximation curved line.

A basic vulcanized rubber material having the compound obtained by removing silica from the above-mentioned first unvulcanized rubber composition is prepared. Besides this basic vulcanized rubber material, a plural of vulcanized rubber materials differing in only crosslink density from the basic vulcanized rubber material are prepared. On the subject of each of the vulcanized rubber materials, by conducting viscoelastic tests, for example, the peak temperature of tan δ of the respective vulcanized rubber materials are measured. The measurement conditions are as previously described.

Figure 9B:
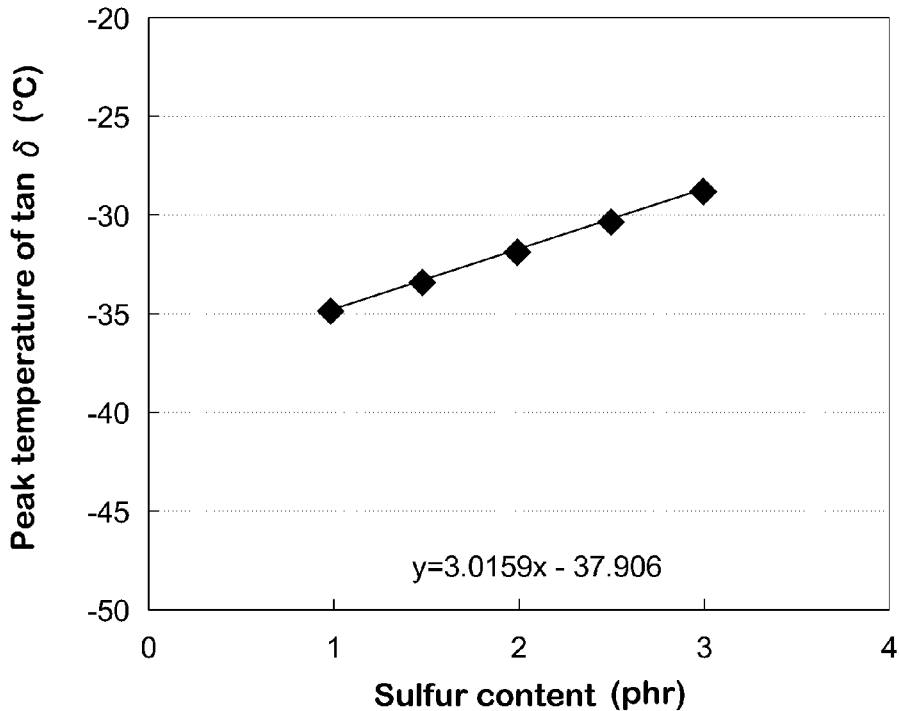

A graph in FIG. 9(b) represents the relation between the peak temperature of tan δ and a crosslink density (which is presented conveniently in a sulfur content) respecting each of the vulcanized rubber materials. In this embodiment, by performing the linear approximation on the subject of the obtained data, calculated is a relation between the peak temperature of tan δ of the vulcanized rubber material and the crosslink density (sulfur content). The approximation straight-line is presented as follows:

$$y=3.0159x-37.906.$$

Also on the subject of this vulcanized rubber material, to improve an accuracy of the approximation straight-line, it is preferable to secure many samples.

The peak temperature of tan δ of the vulcanized rubber material and the crosslink density (sulfur content), identifying the crosslink density (sulfur content) of the vulcanized rubber material having a peak temperature of tan δ is equivalent to a temperature (T3+T2−T1) obtained by adding the above-mentioned difference T2−T1 into the peak temperature T3 of tan δ of the above-mentioned basic vulcanized rubber material (sulfur content: 1 phr). In this embodiment, since the basic vulcanized rubber material has sulfur content of 1 phr, the peak temperature T3 of the tan δ is −28.3565 deg. C using the above-mentioned approximation formula. Accordingly, the temperature (T3+T2−T1) is −28.3565 deg. C. Therefore, when this temperature is substituted into the approximation formula, the value is set about 3.17. This value can be estimated (identified) as a sulfur content (phr) of the vulcanized rubber material at the peak temperature of the tan δ, which is the temperature T3+T2−T1.

The physicality of the vulcanized rubber material of the identified crosslink density (sulfur content) is therefore studied. On the basis of this, the parameter relevant to the physicality of the above-mentioned interface model 5 can be defined.

In this way, in the present embodiment, in a residue containing sulfur of 1 phr, when an amount of rise T2−T1 of the peak temperature of the tan δ in changing the interface bonding agent of from 0 wt % (without any effects of the interface bonding agent, and having a property equivalent to the matrix rubber) to 8 wt % conforms with an amount of rise of the peak temperature of tan δ of the vulcanized rubber in including neither silica nor the interface bonding agent and increasing the amount of composition of sulfur of from 1 phr to some extent (in this example, rising of 2.17 phr), the physicality of the vulcanized rubber is defined as a physicality of the interface model. That is to say, the crosslink density of the interface model resulting from the interface bonding agent of the silica is approximately estimated by use of the sulfur content. In consequence of various tests, it turns out there is a correlation between the amount of rise of the peak temperature of tan δ of the residue caused by containing the interface bonding agent and the amount of rise of the peak temperature of tan δ of the vulcanized rubber caused by sulfur-containing. Therefore, in this way, defining the parameter helps to obtain a higher-accuracy test result.

Therefore, once the above-mentioned vulcanized rubber material is identified, it can measure its various sorts of physicality and define easily the parameter of the interface model 5 on the basis of those values. For example, it is capable of separately forming a crosslink rubber without containing silica so as to have the crosslink density (average crosslink density) obtained in the above-mentioned process; of performing a physicality test again; and of deciding the physicality as a parameter of physicality value of the interface model 5.

Then a deformation condition to deform the rubber material model is set (step S2). In the present embodiment, defined is a condition caused a tensile deformation in the rubber material model 2 by adding an arbitrary average strain speed in the y-direction of FIG. 3. Incidentally, it comes near to stating the obvious that the deformation condition can be variously decided.

Figure 10:
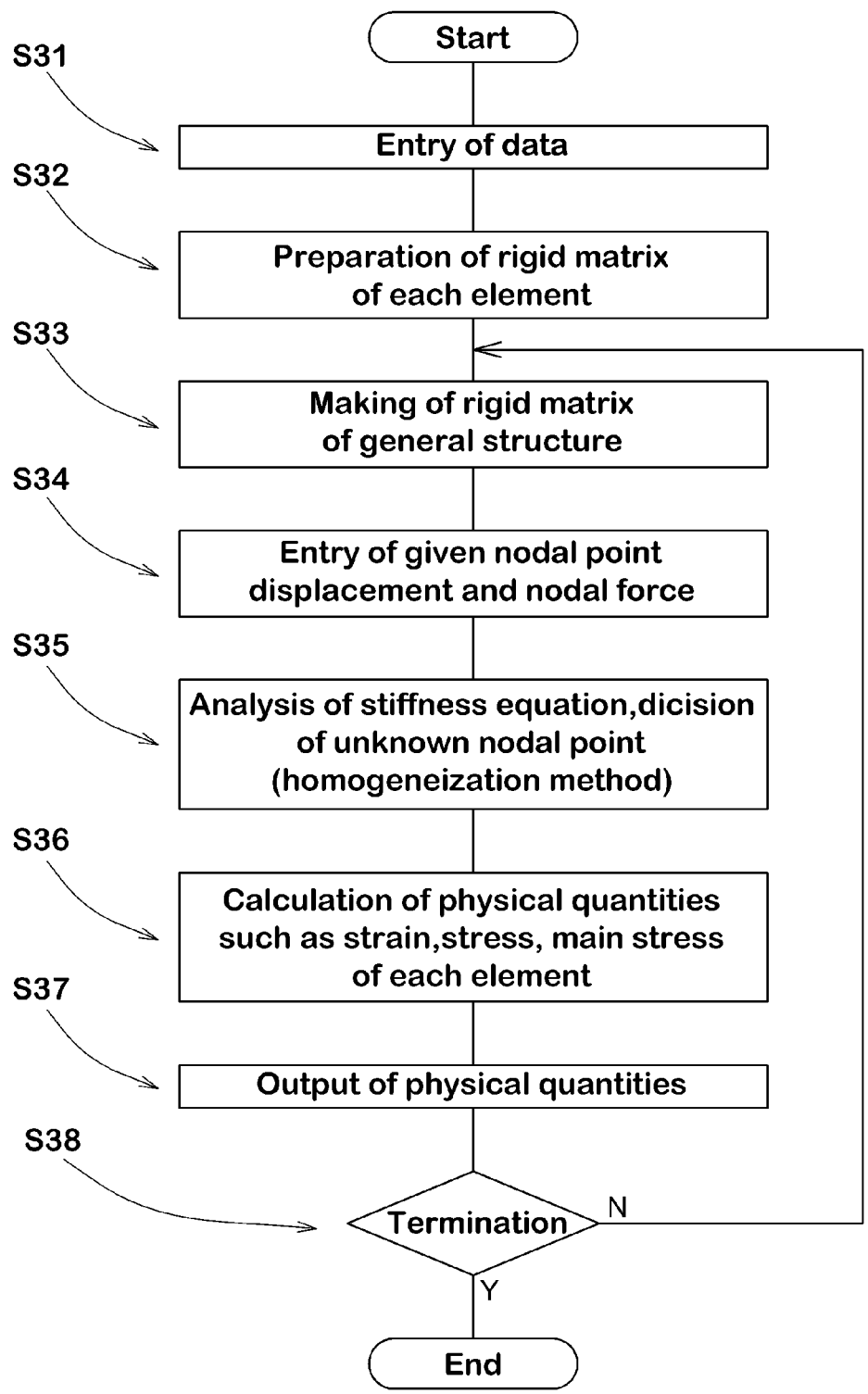
FIG. 10 is a flowchart showing a procedure of the deformation simulation.

In the simulation method of the present embodiment, a deformation simulation using the rubber material model 2 as above defined is conducted (step s3). A concrete operating procedure of the deformation simulation is shown in FIG. 10.

In the deformation simulation, first of all, each kind of data of the rubber material model 2 is entered in a computer device 1 (step s31). The entered data includes information such as a position of a nodal point defined for each element and a material property.

In the computer device 1, a rigidity matrix of each element on the basis of the entered data is prepared (step S32), then the rigidity matrix of general structure is made (step S33). A given nodal point displacement and a nodal force are entered into the rigidity matrix of general structure (step S34); and an analysis of stiffness equation is performed. Then, an unknown nodal point displacement is decided (step S35); and physical quantities such as strain, stress, main stress of each element are calculated and output (step S36 or 37).

In step S38, whether to terminate the calculation is decided, and the steps from the step S32 are repeated when the decision is negative. Such a simulation (deformation calculation) can be performed, for example, with an engineering-related analysis application software by use of the finite element method analysis (LS-MYNA, created and improved by Livermore Software Technology corporation in the U.S.A., for example).

Figure 11:
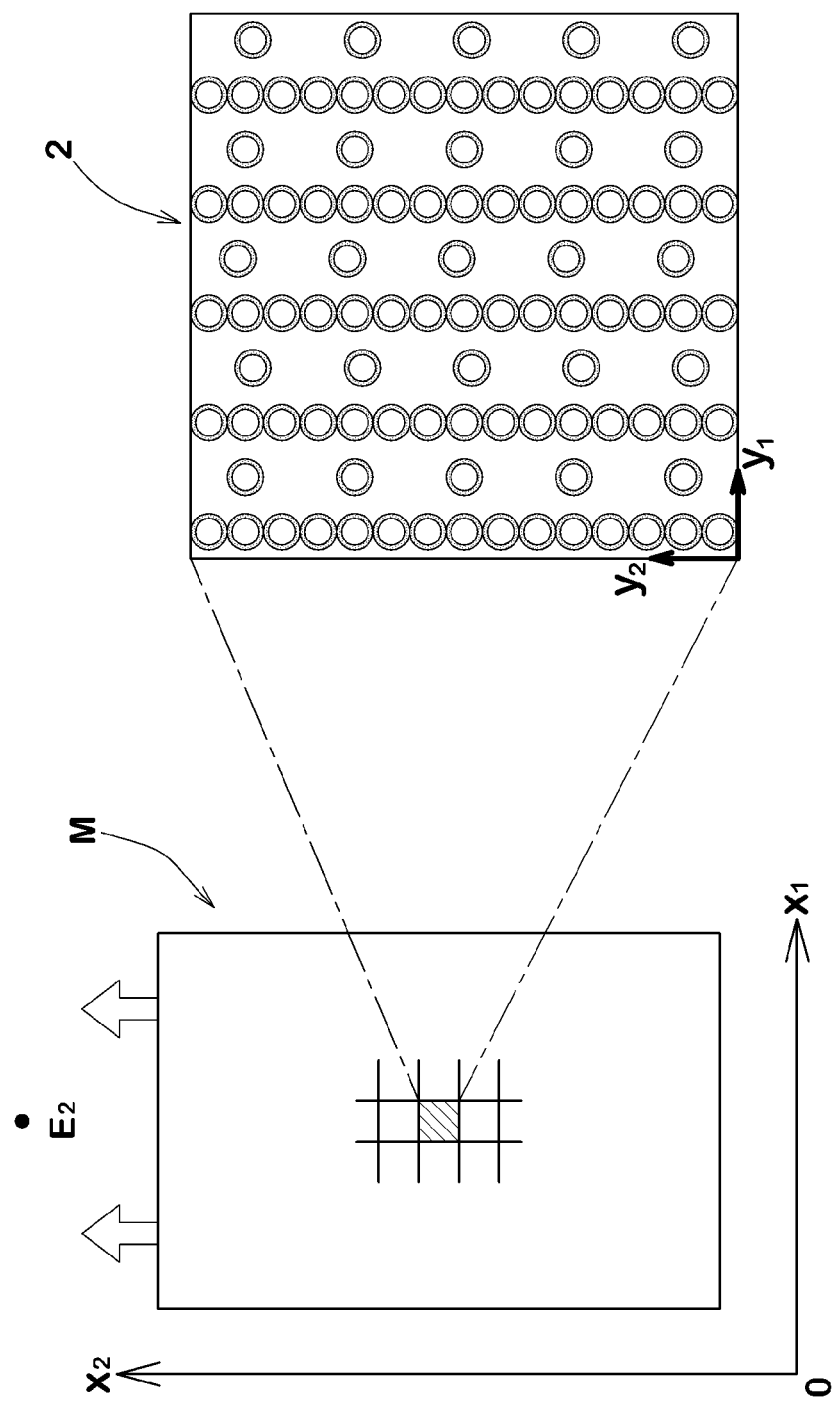
FIG. 11 to showing a relation between the microscopic structure and the overall structure explain a homogeneization method.
Figure 12A:
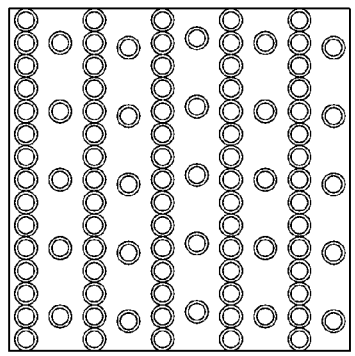
FIG. 12 (a) to FIG. 12 (e) are line drawings of the rubber material model showing Examples and comparative Examples.
Figure 12C:
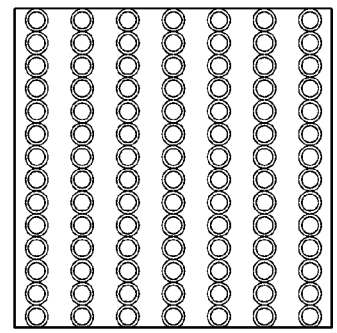
Figure 12B:
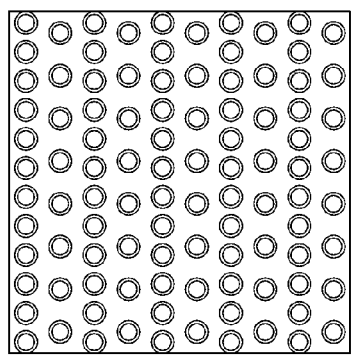
Figure 12D:
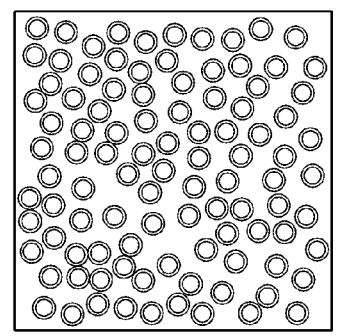
Figure 12E:
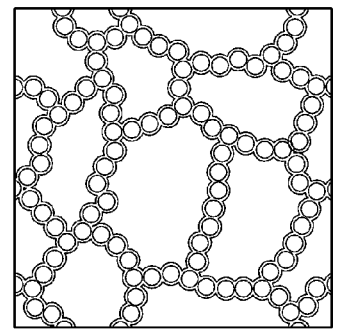

This simulation is conducted on the basis of the homogeneization method (asymptotic evolution homogeneization method). The homogeneization method as showed in FIG. 11 uses two independent indefinite numbers or variable numbers $x_1$ and $y_1$. The $x_1$ represents the whole of rubber material having periodically a microscopic structure (called also as a "unit cell" in the homogeneization method) shown in FIG. 3. And, the $y_1$ represents the above-mentioned microscopic structure. With an asymptotic evolution of the respective independent indefinite numbers or variable numbers in the different scales such as a microscopic scale and a macroscopic scale, the whole rubber material reflected by the model structure of the microscopic structure shown in FIG. 3 can calculate approximately an average dynamic reply.

When the above-mentioned deformation calculation is performed, acquiring needed physical quantities can be obtained from the result (step s4). To study a deformation behavior of the silica compounded rubber, the physical quantities are peculiarly effective a stress-strain curve. And, it is capable to visualize and display a time-oriented deformation state and a distribution of the physical amount of respective elements of the rubber material model 2. At this time, it is preferable to color the respective elements according to the stress.

Then, in the present embodiment, by performing the simulation with the rubber material model 2 comprising the interface model 5, a higher accuracy calculation result can be obtained more than ever (see the after-mentioned Embodiments). It can be estimated that this is because a movement between the silica particles is approximative to the behavior inside the real rubber material, as well as the interfacial behavior between silica and the matrix rubber after experiencing an external force.

Although the especially preferred embodiments of the present invention have been described in detail, various modifications can be made.

EMBODIMENTS (1) Analysis Model:
A whole macroscopic model of a rubber material compounding silica was set, which had periodically models 1 to 5 in the microscopic structure as shown in FIGS. 12 (a) to (e), respectively.

Figure 13:
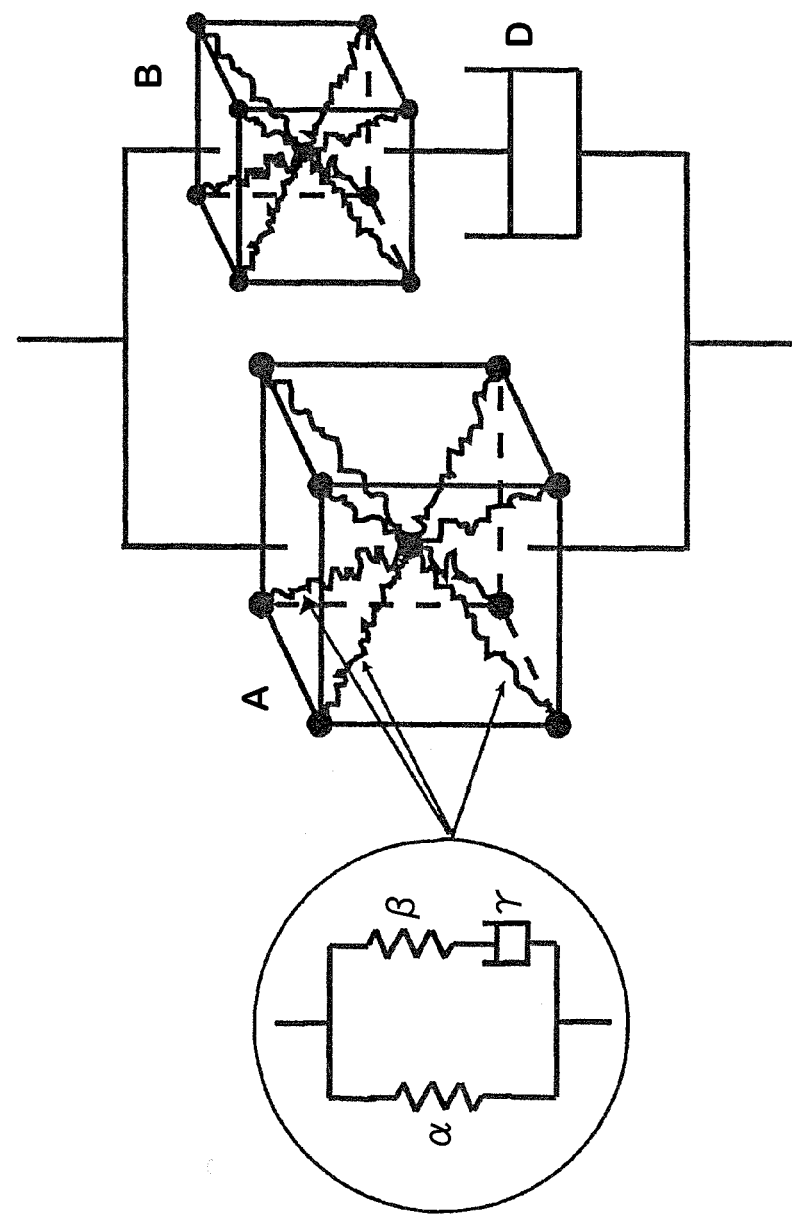
FIG. 13 is a configuration diagram of the eight-chain model of the embodiment.

(2) Specific Constitutive Equation of Eight-Chain Model:

In this embodiment, in order to describe more accurately a viscoelastic behavior of the rubber, as shown in FIG. 13, used were a viscoelastic eight-chain model and a model with damper. A molecular chain of a real rubber had viscosity attributable to friction with peripheral molecular chains. To express this friction, each molecular chain of the eight-chain model A was modeled on a standard model of a spring-damper having viscosity resistance. Therefore, a stress σc occurred when adding an stretch λc in the direction of a line connecting two junction points of the single molecular chain could be expressed with the following formula from the above-mentioned formula (1).

[Number 2]

$$\sigma_c = C_\alpha^R \sqrt{N_\alpha} \, \lambda_c L^{-1}\left(\frac{\lambda_c}{\sqrt{N_\alpha}}\right) + C_\beta^R \sqrt{N_\beta} \frac{\lambda_c}{\lambda_\gamma} L^{-1}\left(\frac{\lambda_\beta}{\sqrt{N_\beta}}\right)$$

$$C_\alpha^R = n_\alpha k_B T$$

$$C_\beta^R = n_\beta k_B T$$

$$n = n_\alpha + n_\beta$$

$n$: number of molecular chains included in the unit $N_\alpha$, $N_\beta$: Segment numbers of molecular chain $\sqrt{N_\alpha}$, $\sqrt{N_\beta}$: Limit stretchs of molecular chain.

When stretches of each of elements of the single molecular chain shown in FIG. 13 were defined as λα, λβ, and λγ, the relation is as follows:

$$\lambda\gamma = \lambda c$$

The other suffixes α, β, and γ correspond to the elements shown in FIG. 13. Incidentally, λc=λβ·λγ.

By applying the strain energy density function w, based on the volume before deformation a corresponding to work per unit volume the stress σc was shown as follows.

[Number 3]

$$\sigma_c = \lambda_c \frac{\partial W}{\partial \lambda_c}$$

From the above-mentioned two formulas, the following equation held identically.

[Number 4]

$$\frac{\partial W_c}{\partial \lambda_c} = C_\alpha^R \sqrt{N_\alpha} \, L^{-1}\left(\frac{\lambda_c}{\sqrt{N_\alpha}}\right) + C_\beta^R \sqrt{N_\beta} \frac{1}{\lambda_\gamma} L^{-1}\left(\frac{\lambda_\beta}{\sqrt{N_\beta}}\right)$$

In the case of the eight-chain model, when the main stretches were defined as $\lambda_1$, $\lambda_2$, and $\lambda_3$, the stretch λc of the molecular chain was expressed as $\sqrt{(\lambda_{12}+\lambda_{22}+\lambda_{32})/3}$; the following formula therefore held.

[Number 5]

$$\frac{\partial \lambda_c}{\partial \lambda_l} = \frac{\lambda_l}{3\lambda_c}$$

The above-mentioned three formulas, a stress $\sigma_i^A$ of the main stretch direction of the eight-chain model A and the stretch $\lambda_i$ were expressed as follows.

[Number 6]

$$\sigma_i^A = \lambda_l \frac{\partial W}{\partial \lambda_\gamma} = \lambda_l \frac{\partial W}{\partial \lambda_c} \frac{\partial \lambda_c}{\partial \lambda_l}$$

$$= \frac{1}{3}\left\{C_{nd}^R \sqrt{N_{\alpha A}} \, L^{-1}\left(\frac{\lambda_{nd}}{\sqrt{N_{\alpha A}}}\right) + C_{\beta A}^R \sqrt{N_{\beta A}} \frac{1}{\lambda_\gamma} L^{-1}\left(\frac{\lambda_{\beta A}}{\sqrt{N_{\beta A}}}\right)\right\} \frac{\lambda_l^2}{\lambda_{\alpha A}}$$

A stress $\sigma_i^B$ of the main stretch direction of the eight-chain model B and the stretch $\lambda_i'$ were expressed as follows.

[Number 7]

$$\sigma_t^R = \frac{1}{3}\left\{C_{\alpha A}^R \sqrt{N_{\alpha B}} \, L^{-1}\left(\frac{\lambda_{\alpha B}}{\sqrt{N_{\alpha B}}}\right)\right\} \frac{\lambda_l^a}{\lambda_{\alpha B}}$$

In this embodiment, used was incompressible rubber material. Therefore, to meet the incompressibility, a hydrostatic pressure (p) was used. At this time, by use of the above-mentioned two formulas, a constitutive equation of the incompressible rubber material was expressed as follows:

$$\sigma_i = \sigma_i^A + \sigma_i^B - p$$

A speed formula of the above-mentioned constitutive equation was shown as follows; and in this embodiment, used was this formula.

[Number 8]

$$\overset{\nabla}{S}_{ij} =$$

$$\frac{1}{3}\left[\left\{C_{\alpha A}^R \sqrt{N_{\alpha A}}\left(\frac{\zeta}{\sqrt{N_{\alpha A}}} - \frac{L}{\lambda_{\alpha A}}\right) + \frac{C_{\beta A}^R \sqrt{N_{\beta A}}}{\lambda_\gamma}\left(\frac{\zeta'}{\lambda_\gamma \sqrt{N_{\beta A}}} - \frac{L'}{\lambda_{\alpha A}}\right)\right\} A_{ij}\right.$$

$$A_{kl}/A_{mm} + \left\{\frac{L C_{\alpha A}^R \sqrt{N_{\alpha A}}}{\lambda_{\alpha A}} + \frac{L' C_{\beta A}^R \sqrt{N_{\beta A}}}{\lambda_{\alpha A}}\right\}(\delta_{ik} A_{jl} + A_{ik}\delta_{jl})\right]$$

$$\dot{\varepsilon}_{kl} - \frac{C_{\beta A}^R \sqrt{N_{\beta A}} \lambda_\gamma}{\lambda_\gamma^2 \sqrt{3 A_{mm}}}\left(L' + \frac{\lambda_\beta \zeta'}{\sqrt{N_{\beta A}}}\right) A_{ij} +$$

$$\frac{1}{3}\left[\left\{C_{\alpha B}^R \sqrt{N_{\alpha B}}\left(\frac{\zeta''}{\sqrt{N_{\alpha B}}} - \frac{L''}{\lambda_{\alpha B}}\right)\right\} A'_{ij} A'_{kl}/A'_{mm} + \right.$$

$$\left.\frac{L'' C_{\alpha B}^R \sqrt{N_{\alpha B}}}{\lambda_{\alpha B}}\{\delta_{ik} A'_{jl} + A'_{ik}\delta_{jl}\}\right](\dot{\varepsilon}_{kl} - \dot{\varepsilon}_{kl}^p) - p\delta_{ij}$$

$\overset{\nabla}{S}_{ij}$: Jaumann speed of Kirchoff stress $\dot{\varepsilon}_{kl}$: Strain rate tensor $\dot{\varepsilon}_{kl}^p$: Viscous strain rate tensor $A_{ij}$: Left Cauchy-Green deformation tensor $L = L^{-1}(\lambda_c/\sqrt{N_\alpha})$ $L' = L^{-1}(\lambda_\beta/\sqrt{N_\beta})$ $L'' = L^{-1}(\lambda_{\alpha B}/\sqrt{N_\alpha} \, B)$ $\zeta = L^2/(1 - L^2 \text{csch}^2 L)$ $\zeta' = L'^2/(1 - L'^2 \text{csch}^2 L')$ $\zeta'' = L''^2/(1 - L''^2 \text{csch}^2 L'')$ (3) Average Segment Number N of the Single Molecular Chain of the Matrix Model:
The following formula was applied.

$$N(\lambda c) = N_0 + f(\lambda c)$$
$$= N_0 + a_0 + a_1 \lambda c + a_2 \lambda c 2$$

An example of how to decide a concrete function of $f(\lambda c)$ was described below. First of all, a change of tangle points associated with the material deformation of the matrix model depended only on $\lambda c$ (stretch). Therefore, the simulation to obtain a stress-strain curve with a rubber without filler of un-filled silica, and the modulus $f(\lambda c)$ was defined so that this result was consistent with a test result of the real rubber without filler. At a first loaded deformation cycle, the number of tangle at the time of loading changed (decreased); and at the time of un-loaded state, the value did not change from the beginning of un-loading. Thus, the modulus of the above-mentioned function $f(\lambda c)$ so that the simulation result was consistent with the real test result. It was defined that, the number of tangle changes irreversibly at the time of re-loading after un-loading once. That is to say, at the time of re-loading, the average segment N was defined to be unchangeable in the deformable region of not more than the maximum stretch obtained at the last loaded deformation cycle. In other word, the number N of the de-loading of the first deformation cycle was identical with the re-loading of the second deformation cycle. Thus, when being over the maximum stretch obtained in the first deformation cycle owing to progressing deformation, the value of N was defined to re-change (decrease). In the present embodiment, a constant part of the above-mentioned formula and the like were defined as follows:

$$a_0 = 1.20$$
$$a_1 = -2.19$$
$$a_2 = 0.99$$

Figure 14:
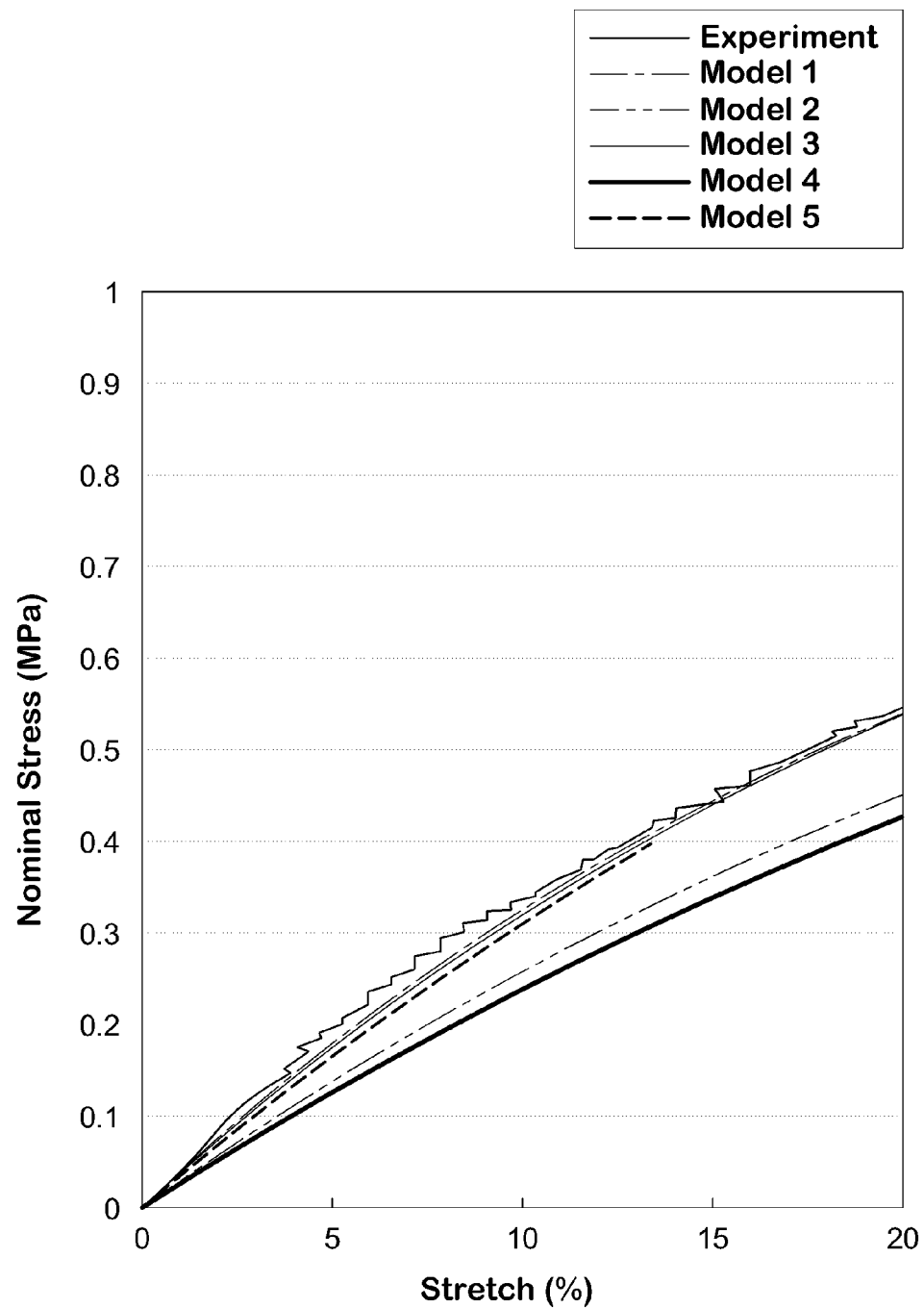
FIG. 14 is a nominal stress-stretch curve line to compare a simulation result to a test result.
Figure 15:
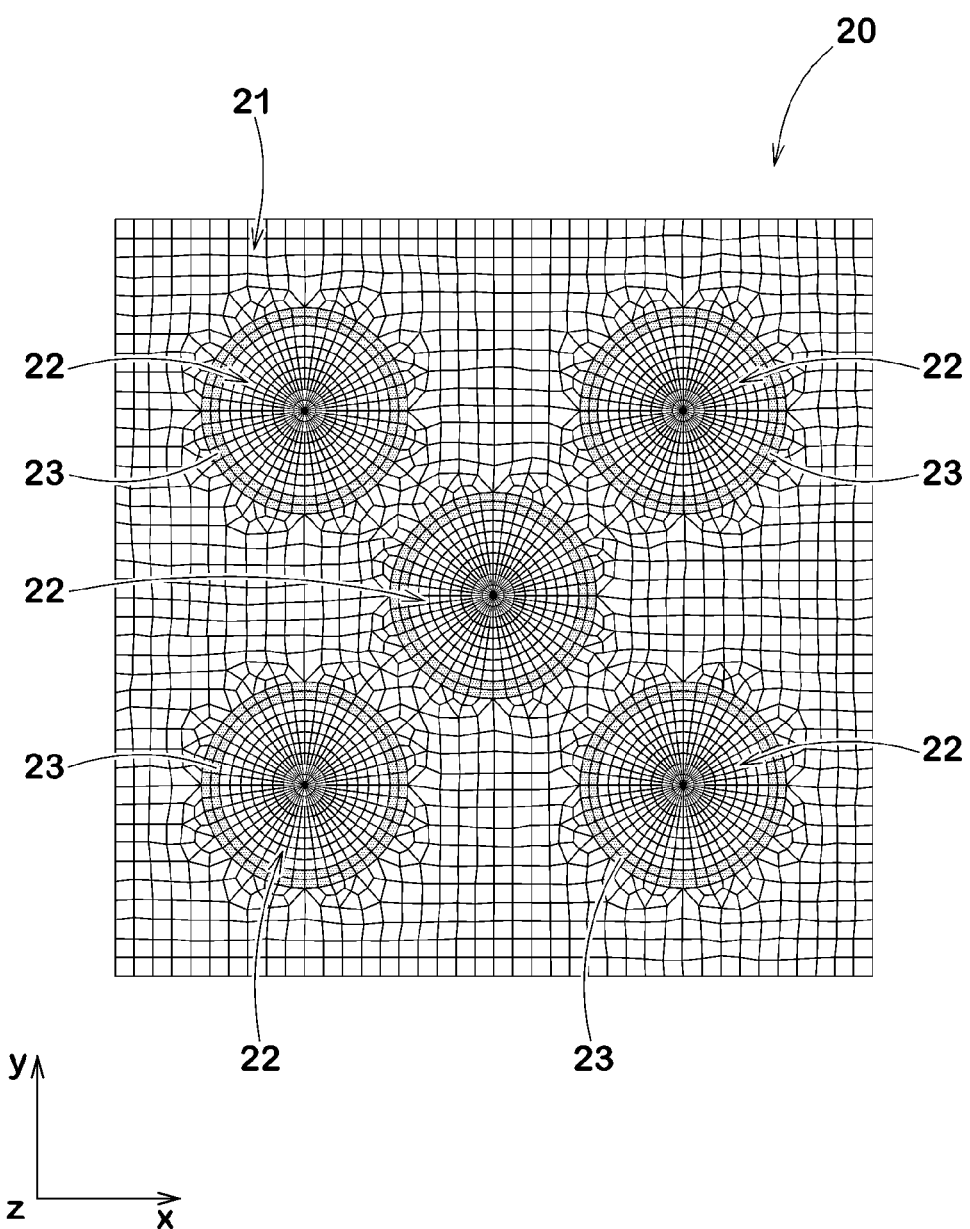
FIG. 15 is a conventional model of the rubber material compounding silica.

[Element A]
$C^R_{\beta A} = 0.22$ MPa
Initial stage segment $N_{A0} = 14$
Total segment number $N_{A\alpha} = 7.54 \times 10^{26}$
[Element B]
$C^R_{\alpha \beta} = 0.22$ MPa
Initial stage segment $N_{\beta 0} = 14$
[Viscoelastic Element]
$C_{1A} = 5.0 \times 10^5$
$C_{2A} = -0.5$
$m_A = 3.5$
$C_{1D} = 3.0 \times 10^5$
$C_{2D} = -0.5$
$m_D = 5.5$
(4) Interface Model:
A constant and the like are set as follows.
$N = N_0$
Initial stage segment number ($N = N_0$): 8.0 (fixed value)
Total segment number $N_A$: $7.54 \times 10^{26}$
Thickness of Interface portion: 10% of diameter of silica model
Width T1 of first connection: 20% of diameter of silica model
Width T2 of second connection: 35% of diameter of silica model
$C_\alpha^{Rs} = 0.385$ MPa (5) Parameter of Silica Model and the Like:
Particle size: identical
Longitudinal elastic modulus of silica model: 100 MPa
Poisson's ratio of silica model: 0.3
Volume content percentage $\mu$ of silica model: 20%
(6) Other Conditions:
Material temperature: T=296 K
$k_B = 1.38066 \times 10^{-29}$
Penalty constant: 100
Content percentage of coupling agent: 8 wt %
(7) Deformation Condition:
To generate a uniform single axis tensile deformation in the above-mentioned macroscopic model, the macroscopic model is accelerated at a constant strain speed 100 mm/min in the direction x2 shown in FIG. 11 to have an stretch of 20%. Not to change it in the thickness direction (in the z-axis direction of FIG. 3), the calculation was conducted with use of the eight-chain model on the basis of the molecular chain reticulation theory.
(8) Calculation Results:
FIG. 14 shows a simulation and test values regarding a stress-stretch curve line of each rubber material model of Examples and Comparative Examples. As is clear from FIG. 14, it was confirmed that the models of Examples had a very high correlation with the test values compared to Reference Examples, respectively. In particular, it was confirmed that the accuracy of the model 1 and the model 3 are particularly well, which extend in a linear fashion along the tensile direction and continuously extending in the entire range of the region of the rubber material model. Meanwhile, it was confirmed that the model of comparative Example, compared to the Example, had a lower correlation was than the test values.

The invention claimed is:
1. A method for simulating a rubber material comprising the steps of:
setting a rubber material model modeled on a rubber material including a matrix rubber, silica, and an interface bonding agent to bond them with numerically analyzable elements;
calculating deformation by setting conditions in said rubber material model; and
acquiring needed physical quantity from said deformation;
calculation, wherein said rubber material model comprises;
a matrix model modeled on the matrix rubber;
a plurality of silica models modeled on said silica arranged in said matrix model; and
an interface model surrounding annularly each of said silica models and having a harder physical property than said matrix model, wherein said rubber material model comprises a coupled body formed by coupling a plural of said silica models via said interface model, and
wherein said step of setting the rubber material model comprises a parameter determination process to determine a parameter of physicality in said interface model, the parameter determination process comprising the steps of:
preparing at least a first unvulcanized rubber composition having the same compound as said rubber material model of an analysis object, and a second unvulcanized rubber composition having a compound excluding an interface bonding agent from the first unvulcanized rubber composition;
obtaining first and second residues after removing the matrix rubber from the first and second unvulcanized rubber compositions, respectively, by immersing the first and second unvulcanized rubber composition into a solvent;

estimating a difference between two peak temperatures T2–T1 by measuring at least a peak temperature T2 of loss tan δ of said second residue and a peak temperature T1 of loss tan δ of said first residue;

preparing a basic vulcanized rubber material having a compound excluding silica from said first unvulcanized rubber composition, and different kinds of vulcanized rubber materials having a difference only in crosslink density from the basic vulcanized rubber material;

obtaining a relation between said peak temperatures T2 and T1 of loss tan δ of the vulcanized rubber material and the crosslink density by measuring each of the peak temperatures T2 and T1 of loss tan δ of said vulcanized rubber materials;

specifying a crosslink density of the vulcanized rubber material having a peak temperature of loss tan δ is equivalent to a temperature obtained by adding said difference between two peak temperatures T2–T1 into a peak temperature T3 of loss tan δ of said basic vulcanized rubber material from said relation; and defining said parameter of said interface model on the basis of the physicality of the vulcanized rubber material of said specified crosslink density.

2. The method for simulating the rubber material as set forth in claim 1, wherein said coupled body extends continuously with respect to an arbitral direction of axis in the entire range of the region of the rubber material model.

* * * * *